United States Patent
Slapak

(10) Patent No.: US 8,063,255 B2
(45) Date of Patent: Nov. 22, 2011

(54) PROCESS FOR THE RECOVERY OF MONOETHYLENE GLYCOL

(75) Inventor: Mathias Jozef Paul Slapak, Amsterdam (NL)

(73) Assignee: Shell Oil Company, Houston, TX (US)

( * ) Notice: Subject to any disclaimer, the term of this patent is extended or adjusted under 35 U.S.C. 154(b) by 291 days.

(21) Appl. No.: 12/576,700

(22) Filed: Oct. 9, 2009

(65) Prior Publication Data

US 2010/0094065 A1    Apr. 15, 2010

(30) Foreign Application Priority Data

Oct. 9, 2008  (EP) .................................. 08166267

(51) Int. Cl.
  *C07C 27/28*  (2006.01)
  *C07C 27/30*  (2006.01)
  *C07C 27/32*  (2006.01)
(52) U.S. Cl. ....................................... 568/868; 568/867
(58) Field of Classification Search .................. 568/621, 568/680, 699, 867, 868
  See application file for complete search history.

(56) References Cited

U.S. PATENT DOCUMENTS

| | | | | |
|---|---|---|---|---|
| 4,349,417 A * | 9/1982 | Rebsdat et al. | ................. | 203/33 |
| 4,830,712 A * | 5/1989 | Crandall et al. | ................. | 203/35 |
| 6,080,897 A | 6/2000 | Kawabe | ........................ | 568/858 |
| 6,187,972 B1 | 2/2001 | Kawabe et al. | ................. | 568/858 |
| 6,514,388 B1 * | 2/2003 | Adrian et al. | ................... | 203/18 |
| 6,605,192 B1 * | 8/2003 | Theis et al. | ........................ | 203/3 |
| 2008/0081933 A1 * | 4/2008 | Bastings et al. | .............. | 568/858 |

FOREIGN PATENT DOCUMENTS

| | | |
|---|---|---|
| EP | 776890 | 6/1997 |
| EP | 1484300 | 12/2004 |

* cited by examiner

*Primary Examiner* — Brian J Davis

(57) ABSTRACT

A process for recovering monoethylene glycol from a catalyst bleed stream is disclosed. The process comprises combining the catalyst bleed stream with a heavies stream comprising at least 40 wt % diethylene glycol, to provide a combined stream and distilling the combined stream to provide a first stream comprising monoethylene glycol and a second stream comprising diethylene glycol.

10 Claims, 2 Drawing Sheets

PROCESS FOR THE RECOVERY OF MONOETHYLENE GLYCOL

FIELD OF THE INVENTION

The present invention relates to a process for the recovery of monoethylene glycol from a catalyst bleed stream.

BACKGROUND OF THE INVENTION

Monoethylene glycol is used as a raw material in the manufacture of polyester fibres, polyethylene terephthalate (PET) plastics and resins. It is also incorporated into automobile antifreeze liquids.

Monoethylene glycol is typically prepared from ethylene oxide, which is in turn prepared from ethylene. Ethylene and oxygen are passed over a silver oxide catalyst, producing a product stream comprising ethylene oxide, carbon dioxide, ethylene, oxygen and water. The product stream is supplied to an ethylene oxide absorber and the ethylene oxide is absorbed by a recirculating solvent stream.

The solvent stream leaving the ethylene oxide absorber is supplied to an ethylene oxide stripper, wherein ethylene oxide is removed as a vapour stream. The ethylene oxide obtained from the ethylene oxide stripper can be purified for storage and sale or can be further reacted to provide monoethylene glycol.

In the process described in U.S. Pat. No. 6,080,897 and U.S. Pat. No. 6,187,972, ethylene oxide is catalytically reacted with carbon dioxide to produce ethylene carbonate. The ethylene carbonate is subsequently hydrolysed; the reaction of ethylene carbonate with water produces an ethylene glycol product stream. The product stream from the hydrolysis step is subjected to dehydration to remove water. The dehydrated stream is subjected to distillation wherein a glycol stream is removed from the top of the distillation column and a catalyst solution is removed from the bottom of the column. The catalyst solution is recycled to the carboxylation reactor.

EP 776 890 discloses a similar process wherein the product stream from the hydrolysis reactor is separated into a glycol stream and a catalyst solution. The catalyst solution is recycled to the ethylene oxide absorber. A portion of the catalyst solution is discharged as a catalyst bleed stream to avoid accumulation of heavy components such as diethylene glycol.

In addition to diethylene glycol, a catalyst bleed stream is likely to comprise catalyst degradation products, other impurities and monoethylene glycol. It is desirable to recover the monoethylene glycol from the catalyst bleed stream to increase the yield of the product. The present inventors have sought to provide a process that can be used to recover monoethylene glycol from a catalyst bleed stream. Desirably the process is integrated into the monoethylene glycol manufacturing process.

SUMMARY OF THE INVENTION

Accordingly, the present invention provides a process for recovering monoethylene glycol from a catalyst bleed stream, comprising the steps of:
a) combining the catalyst bleed stream, and optionally further bleed streams, with a heavies stream comprising at least 40 wt % diethylene glycol, to provide a combined stream;
b) optionally dehydrating the combined stream; and
c) providing the combined stream from step (a) or step (b) to a distillation column and removing from the distillation column a first stream comprising monoethylene glycol and a second stream comprising diethylene glycol.

By combining the catalyst bleed stream with a "heavies" stream comprising at least 40 wt % diethylene glycol and subsequently distilling, it is possible to recover monoethylene glycol as a first stream from the top of the distillation column and to concentrate heavy impurities, salts and catalyst as a second stream from the bottom of the distillation column. It is preferable to bleed (and dispose of) the catalyst stream in a liquid that is primarily the heavy impurities compared to bleeding (and disposing of) the catalyst stream in a liquid that is primarily monoethylene glycol because the monoethylene glycol has a higher value than the heavy impurities. By carrying out the process of the invention for recovering monoethylene glycol in an ethylene glycol manufacturing plant, the inventors believe it is possible to improve the overall yield of monoethylene glycol for the ethylene glycol manufacturing plant.

DETAILED DESCRIPTION OF THE INVENTION

Figure 1:
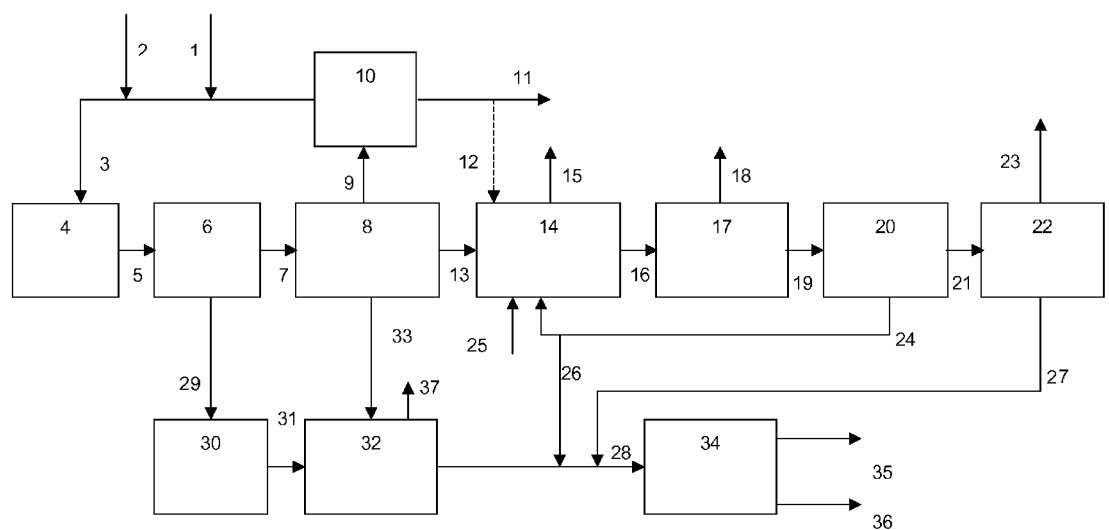
FIG. 1 is a schematic diagram showing a process according to an embodiment of the invention.

In an ethylene glycol manufacturing plant, ethylene oxide is reacted, optionally via ethylene carbonate, to give monoethylene glycol. One or more homogeneous catalysts are used to catalyse the reaction step(s). The one or more homogeneous catalysts are separated from the glycol product stream and are returned to the reaction zones via the catalyst recycle stream. A catalyst bleed stream, comprising monoethylene glycol, is taken from the catalyst recycle stream. Expressed as a weight percentage of the catalyst recycle stream, preferably from 0.0001 wt % to 10 wt %, more preferably from 0.001 to 1 wt % of the catalyst recycle stream is removed as the catalyst bleed stream.

In one embodiment of the invention, the process for recovering monoethylene glycol is carried out in an ethylene glycol manufacturing plant substantially as described in U.S. Pat. No. 6,080,897 and U.S. Pat. No. 6,187,972 which are herein incorporated by reference in their entirety. The plant comprises an ethylene oxide reactor (wherein ethylene is reacted with oxygen to provide a product stream comprising ethylene oxide), an ethylene oxide absorber, (wherein ethylene oxide is absorbed by a recirculating solvent stream), an ethylene oxide stripper (wherein ethylene oxide is removed as a vapour stream), a carboxylation reactor (wherein ethylene oxide is reacted with carbon dioxide in the presence of a homogeneous catalyst to provide ethylene carbonate), a hydrolysis reactor (wherein ethylene carbonate is reacted with water in the presence of a homogeneous catalyst to provide ethylene glycol) and apparatus for purifying the glycol product stream. The homogeneous catalyst(s) for carboxylation and hydrolysis are separated from the glycol product stream and are recycled to the carboxylation and hydrolysis reactors. Preferably the catalyst(s) is/are recycled to the carboxylation reactor, and is/are therefore present in the stream from the carboxylation reactor that is supplied to the hydrolysis reactor.

In another embodiment of the invention, the process for recovering monoethylene glycol is carried out in an ethylene glycol manufacturing plant comprising an ethylene oxide reactor, an ethylene oxide absorber and an ethylene oxide stripper as outlined above. However, the ethylene oxide from the stripper is directly provided to a hydrolysis reactor wherein ethylene oxide is reacted with water, in the presence of a homogeneous catalyst, to provide ethylene glycol. The reaction does not proceed via ethylene carbonate. The plant further comprises apparatus for purifying the glycol product stream. The hydrolysis catalyst is separated from the glycol product stream and is recycled to the hydrolysis reactor. This embodiment is not preferred because higher selectivity is typically obtained when the reaction proceeds via the ethylene carbonate intermediate.

In yet another embodiment of the invention, the process is carried out in an ethylene glycol manufacturing plant wherein the ethylene oxide absorber acts both as an absorber, absorbing ethylene oxide in a recirculating solvent stream, and as reactor, converting ethylene oxide to ethylene carbonate and/or ethylene glycol in the presence of one or more homogeneous catalysts. The plant comprises an ethylene oxide reactor, the ethylene oxide absorber, optionally further reactors wherein additional carboxylation and hydrolysis occur, and apparatus for purifying the reaction products. The catalyst(s) for carboxylation and hydrolysis are separated from the glycol product stream and are recycled to the ethylene oxide absorber.

Homogeneous catalysts that are known to promote carboxylation include alkali metal halides such as potassium iodide and potassium bromide, and halogenated organic phosphonium or ammonium salts such as tributylmethylphosphonium iodide, tetrabutylphosphonium iodide, triphenylmethylphosphonium iodide, triphenylpropylphosphonium bromide, triphenylbenzylphosphonium chloride, tetraethylammonium bromide, tetramethylammonium bromide, benzyltriethylammonium bromide, tetrabutylammonium bromide and tributylmethylammonium iodide. Homogeneous catalysts that are known to promote hydrolysis include basic alkali metal salts such as potassium carbonate, potassium hydroxide and potassium bicarbonate, or alkali metal metalates such as potassium molybdate. It is possible that a catalyst may promote both carboxylation and hydrolysis, but it is preferred to use different catalysts to promote carboxylation and hydrolysis. Preferred homogeneous catalyst systems include a combination of potassium iodide and potassium carbonate, and a combination of potassium iodide and potassium molybdate.

The catalyst bleed stream is combined with a heavies stream comprising at least 40 wt % diethylene glycol, to provide a combined stream. The heavies stream preferably comprises at least 60 wt % diethylene glycol. The heavies stream may also comprise higher glycols such as triethylene glycol, metal salts, catalyst degradation products, esters and aldehydes. The heavies stream is preferably the bottoms stream from a monoethylene glycol recycle column. In a typical monoethylene glycol purification process, a crude glycol stream is sent to a monoethylene glycol purification column where finished monoethylene glycol is taken off as a side stream and the top stream is recycled. The bottom stream is fed to a monoethylene glycol recycle column for further recovery of monoethylene glycol. The bottom stream from this recycle column is desirably combined with the catalyst bleed stream in the process of the present invention.

Preferably the entire catalyst bleed stream is combined with the entire heavies stream to provide the combined stream, although it is possible that one or both of the catalyst bleed stream and the heavies stream are divided such that only part of the catalyst bleed stream or part of the heavies stream is incorporated into the combined stream.

In an embodiment of the invention, further bleed streams that comprise monoethylene glycol are combined with the catalyst bleed stream and the heavies stream to provide the combined stream. The further bleed streams are preferably a quench bleed stream and/or a glycol bleed stream.

A quench bleed stream is derived from the quench section of an ethylene glycol manufacturing plant. A product gas stream comprising ethylene oxide, produced by the reaction of ethylene and oxygen in an ethylene oxide reactor, is preferably provided to a quench section before it is supplied to an ethylene oxide absorber. In the quench section the product gas stream is contacted with a cooled, recirculating aqueous quench stream and preferably a basic solution is continuously added to the recirculating quench stream. A quench bleed is withdrawn from the quench section, preferably from the recirculating aqueous solution. The quench bleed typically comprises water, ethylene oxide, ethylene glycol, salts and other impurities like esters, acids and aldehydes. Before it is combined with the catalyst bleed stream and the heavies stream, the quench bleed is preferably subjected to hydrolysis such that ethylene oxide in the quench bleed stream is converted to ethylene glycol, and is preferably subjected to subsequent concentration or dehydration. Preferably the entire dehydrated quench bleed stream is combined with the catalyst bleed stream and the heavies stream to provide the combined stream, although it is possible that a portion of the quench bleed stream is incorporated into the combined stream.

In ethylene glycol manufacturing plants where the ethylene oxide absorber is functioning as an absorber only (i.e. it is not also functioning as a reactor), lean absorbent is supplied to the absorber to absorb ethylene oxide and fat absorbent, comprising ethylene oxide, is withdrawn from the absorber. Preferably a slip stream is taken from the lean absorbent to avoid the build up glycols in the lean absorbent, and this is known as the glycol bleed stream. Preferably the entire glycol bleed stream is concentrated or dehydrated and combined with the catalyst bleed stream and the heavies stream to provide the combined stream, although it is possible that a portion of the glycol bleed stream is incorporated into the combined stream.

In one embodiment of the invention, the combined stream is dehydrated before it is provided to the distillation column in step (c). Dehydration is preferred if the combined stream comprises significant quantities of water (e.g. greater than 40 wt % water) and especially if a quench bleed or glycol bleed that has not been dehydrated is incorporated into the combined stream.

The combined stream is provided to a distillation column. Preferably the distillation column is a vacuum column with a pressure in the range of from 0.1 to 500 mbar. A first stream comprising monoethylene glycol is removed from or near the top of the distillation column. Preferably the first stream is substantially pure monoethylene glycol (e.g. at least 95 wt % monoethylene glycol). The first stream is preferably sent to the glycol purification section of an ethylene glycol manufacturing plant, e.g. to a dehydrator column or to a monoethylene glycol purification column. Alternatively, the first stream may be sent to a product tank. A second stream comprising diethylene glycol is removed from or near the bottom of the distillation column. In addition to diethylene glycol the second stream is likely to comprise higher glycols (e.g. triethylene glycol), catalyst degradation products and other impurities. Preferably the second stream is worked up to recover diethylene glycol and heavy glycols or is incinerated.

FIG. 1 shows a preferred embodiment of the process of the invention. Oxygen (1) and ethylene (2) are supplied to a recycle gas stream (3). The recycle gas stream (3) is supplied to an ethylene oxide reactor (4), wherein ethylene reacts with oxygen to provide ethylene oxide. An ethylene oxide containing gaseous product stream (5) is supplied to the quench section (6), wherein the gases are cooled and impurities are removed by contacting the gas stream with a recirculating aqueous stream. A quenched gaseous stream (7) is supplied from the quench section (6) to the ethylene oxide absorption and stripping section (8), wherein ethylene oxide is absorbed into an aqueous absorbent and is subsequently removed as a vapour stream. The overhead gases (9) from the ethylene oxide absorption are supplied to a carbon dioxide removal unit (10). Carbon dioxide is removed as a carbon dioxide bleed stream (11) and is optionally supplied as make-up carbon dioxide (12) for the carboxylation reaction. The overhead gases that are not removed in the carbon dioxide removal section (10) are recycled to the ethylene oxide reactor (4) as the recycle gas stream (3).

A stream (13) of ethylene oxide and water is withdrawn from the stripping section and is fed to the carboxylation and hydrolysis reactors (14). Make-up carbon dioxide (12) is optionally supplied to the carboxylation reactors. Within the carboxylation reactors, ethylene oxide reacts with carbon dioxide in the presence of a homogeneous carboxylation catalyst, to provide ethylene carbonate. Within the hydrolysis reactors, ethylene carbonate (and possibly also ethylene oxide) reacts with water in the presence of a homogeneous hydrolysis catalyst, to provide monoethylene glycol. A carbon dioxide bleed stream (15) is removed from the reactors (14). A reactor product stream (16) comprising monoethylene glycol is supplied to a glycol dehydration unit (17). Water (18) is removed from the dehydration unit. A dehydrated stream (19) consisting mainly of glycols and the homogeneous catalysts is supplied to a catalyst separation unit (20). A product stream (21) consisting mainly of glycols is supplied to a glycol purification unit (22). Monoethylene glycol product (23) is withdrawn from the glycol purification unit (22).

A catalyst recycle stream (24) is withdrawn from the catalyst separation unit (20) and is supplied to the carboxylation reactors. Fresh catalyst (25) can also be supplied to the carboxylation reactors. A catalyst bleed stream (26) is withdrawn from the catalyst recycle stream (24). A heavies stream (27) consisting mainly of diethylene glycol is withdrawn from the glycol purification unit (22).

A quench bleed stream (29) is withdrawn from the quench unit (6) and is supplied to hydrolysis unit (30), wherein ethylene oxide in the quench bleed stream is converted to ethylene glycol. The hydrolysed quench bleed stream (31) is supplied to a dehydrator (32), wherein water (37) is removed. A glycol bleed stream (33) is withdrawn from the absorption and stripping unit (8), specifically from the lean absorbent that is supplied to the ethylene oxide absorber. The glycol bleed stream (33) is also supplied to the dehydrator (32). The stream from the dehydrator (32) is combined with the catalyst bleed stream (26) and the heavies stream (27) to form the combined stream (28).

The combined stream (28) is supplied to a distillation column (34). Monoethylene glycol (35) is removed from the top of the column. A stream (36) comprising diethylene glycol, salts, impurities and catalyst degradation products is removed from the bottom of the column.

Figure 2:
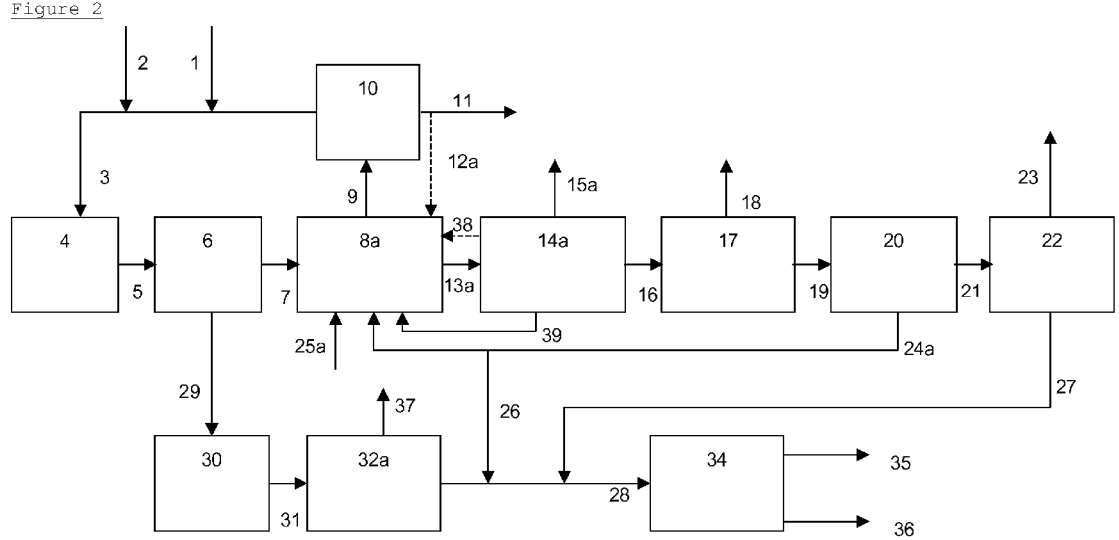
FIG. 2 is a schematic diagram showing a process according to an alternative embodiment of the invention.

FIG. 2 shows another preferred embodiment of the process of the invention. Most features are similar to those shown in FIG. 1. However, the quenched gaseous stream (7) is supplied from the quench section to the ethylene oxide absorption and reaction unit (8a), wherein ethylene oxide is absorbed into an aqueous absorbent and reacts in the presence of carboxylation catalyst and hydrolysis catalyst to provide ethylene carbonate and ethylene oxide. A stream (13a) comprising ethylene oxide, ethylene carbonate and ethylene glycol is supplied to carboxylation and hydrolysis finishing reactors (14a), wherein further reaction of ethylene oxide to ethylene carbonate and ethylene carbonate to ethylene glycol takes place. Make-up carbon dioxide (12a) is optionally supplied to the ethylene oxide absorption and reaction unit (8a). A carbon dioxide bleed stream (15a) is removed from the finishing reactors (14a). The catalyst recycle stream (24a) is supplied from the catalyst separation unit (20) to the ethylene oxide absorption and reaction unit (8a). Fresh catalyst (25a) is also supplied to the ethylene oxide absorption and reaction unit.

Optionally carbon dioxide (38) can be recycled from the finishing reactors (14a) to the ethylene oxide absorption and reaction unit (8a). Absorbent (39) is recycled from the finishing reactors to the ethylene oxide absorption and reaction unit (8a).

There is no glycol bleed stream in this embodiment, so the combined stream (28) is made up of the catalyst bleed stream (26), the heavies stream (27) and the quench bleed that has undergone hydrolysis and dehydration.

The invention claimed is:

1. A process for recovering monoethylene glycol from a catalyst bleed stream, comprising the steps of:
    a) combining the catalyst bleed stream, and optionally further bleed streams, with a heavies stream comprising at least 40 wt % diethylene glycol, to provide a combined stream;
    b) optionally dehydrating the combined stream; and
    c) providing the combined stream from step (a) or step (b) to a distillation column and removing from the distillation column a first stream comprising monoethylene glycol and a second stream comprising diethylene glycol.

2. The process of claim 1 wherein the catalyst bleed stream and at least one further bleed stream are combined with the heavies stream and the at least one further bleed stream is a quench bleed stream and/or a glycol bleed stream.

3. The process of claim 1 wherein the distillation column is a vacuum column with a pressure in the range of from 0.1 to 500 mbar.

4. The process of claim 1 wherein the first stream comprises at least 95 wt % monoethylene glycol, based upon the weight of the first stream.

5. A process for manufacturing monoethylene glycol, wherein ethylene oxide is reacted in the presence of one or more homogeneous catalysts in a reaction zone, optionally via ethylene carbonate, to give monoethylene glycol; wherein the one or more homogeneous catalysts are separated from a glycol product stream and are returned to the reaction zone via a catalyst recycle stream; wherein a catalyst bleed stream comprising monoethylene glycol is taken from the catalyst recycle stream; and wherein monoethylene glycol is recovered from the catalyst bleed stream by a process which comprises the steps of:
    a) combining the catalyst bleed stream, and optionally further bleed streams, with a heavies stream comprising at least 40 wt % diethylene glycol, to provide a combined stream;
    b) optionally dehydrating the combined stream; and
    c) providing the combined stream from step (a) or step (b) to a distillation column and removing from the distillation column a first stream comprising monoethylene glycol and a second stream comprising diethylene glycol.

6. The process of claim 5 wherein the monoethylene glycol is purified in a monoethylene glycol recycle column and wherein the heavies stream is the bottoms stream from the monoethylene glycol recycle column.

7. The process of claim 5 wherein a product stream comprising ethylene oxide, produced by the reaction of ethylene and oxygen in an ethylene oxide reactor, is provided to a quench section before it is supplied to an ethylene oxide absorber; wherein a quench bleed is withdrawn from the quench section and is subjected to hydrolysis, providing a hydrolysed quench bleed stream; and wherein the hydrolysed quench bleed stream is optionally concentrated or dehydrated and is combined with the catalyst bleed stream and the heavies stream.

8. The process of claim 5 wherein lean absorbent is supplied to an ethylene oxide absorber; wherein a glycol bleed stream is withdrawn from the lean absorbent; and wherein the glycol bleed stream is optionally concentrated or dehydrated and is combined with the catalyst bleed stream and the heavies stream.

9. The process of claim 5 wherein the distillation column is a vacuum column with a pressure in the range of from 0.1 to 500 mbar.

10. The process of claim 5 wherein the first stream comprises at least 95 wt % monoethylene glycol, based upon the weight of the first stream.

* * * * *